(12) United States Patent
Bar-Tal et al.

(10) Patent No.: US 8,280,189 B2
(45) Date of Patent: Oct. 2, 2012

(54) DISTORTION-IMMUNE POSITION TRACKING USING REDUNDANT MEASUREMENTS

(75) Inventors: Meir Bar-Tal, Zichron Ya'acov (IL); Assaf Govari, Haifa (IL)

(73) Assignee: Biosense Webster, Inc., Diamond Bar, CA (US)

( * ) Notice: Subject to any disclaimer, the term of this patent is extended or adjusted under 35 U.S.C. 154(b) by 0 days.

(21) Appl. No.: 13/164,141

(22) Filed: Jun. 20, 2011

(65) Prior Publication Data

US 2011/0251815 A1    Oct. 13, 2011

Related U.S. Application Data

(63) Continuation of application No. 11/462,733, filed on Aug. 7, 2006, now Pat. No. 8,082,020.

(51) Int. Cl.
*G06K 9/32* (2006.01)

(52) U.S. Cl. ............... 382/294; 702/95; 324/207.12; 600/12

(58) Field of Classification Search .............. 382/294; 702/95; 324/207.12
See application file for complete search history.

(56) References Cited

U.S. PATENT DOCUMENTS

| | | |
|---|---|---|
| 5,391,199 A | 2/1995 | Ben-Haim |
| 5,443,489 A | 8/1995 | Ben-Haim |
| 5,654,864 A | 8/1997 | Ritter et al. |
| 6,147,480 A | 11/2000 | Osadchy et al. |
| 6,172,499 B1 | 1/2001 | Ashe |
| 6,239,724 B1 | 5/2001 | Doron et al. |
| 6,332,089 B1 | 12/2001 | Acker et al. |
| 6,335,617 B1 | 1/2002 | Osadchy et al. |
| 6,373,240 B1 | 4/2002 | Govari |
| 6,400,139 B1 | 6/2002 | Khalfin et al. |
| 6,493,573 B1 | 12/2002 | Martinelli et al. |
| 6,618,612 B1 | 9/2003 | Acker et al. |
| 6,690,963 B2 | 2/2004 | Ben-Haim et al. |
| 6,755,816 B2 | 6/2004 | Ritter et al. |
| 2002/0065455 A1 | 5/2002 | Ben-Haim et al. |
| 2003/0120150 A1 | 6/2003 | Govari |
| 2003/0139895 A1 | 7/2003 | Lescourret |
| 2004/0068178 A1 | 4/2004 | Govari |
| 2004/0102696 A1 | 5/2004 | Govari |
| 2004/0207389 A1 | 10/2004 | Nieminen et al. |
| 2005/0246122 A1 | 11/2005 | Jones et al. |
| 2006/0122497 A1 | 6/2006 | Glossop |
| 2006/0170417 A1 | 8/2006 | Rodgers et al. |

FOREIGN PATENT DOCUMENTS

| | | |
|---|---|---|
| WO | 96/05768 A1 | 2/1996 |
| WO | 2004/091391 A1 | 10/2004 |
| WO | 2005/082247 A1 | 9/2005 |
| WO | 2006/054295 A1 | 5/2006 |

*Primary Examiner* — Matthew Bella
*Assistant Examiner* — Ruiping Li
(74) *Attorney, Agent, or Firm* — Louis J. Capezzuto

(57) ABSTRACT

A method for tracking a position of an object includes using a field sensor associated with the object to measure field strengths of magnetic fields generated by two or more field generators, wherein a measurement of at least one of the field strengths is subject to a distortion. Rotation-invariant location coordinates of the object are calculated responsively to the measured field strengths. Corrected location coordinates of the object are determined by applying to the rotation-invariant location coordinates a coordinate correcting function so as to adjust a relative contribution of each of the measured field strengths to the corrected location coordinates responsively to the distortion in the measured field strengths.

16 Claims, 3 Drawing Sheets

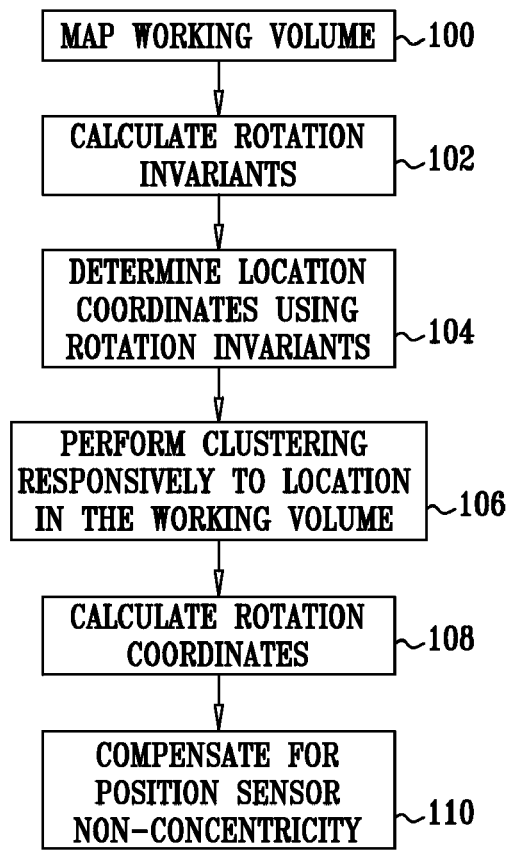
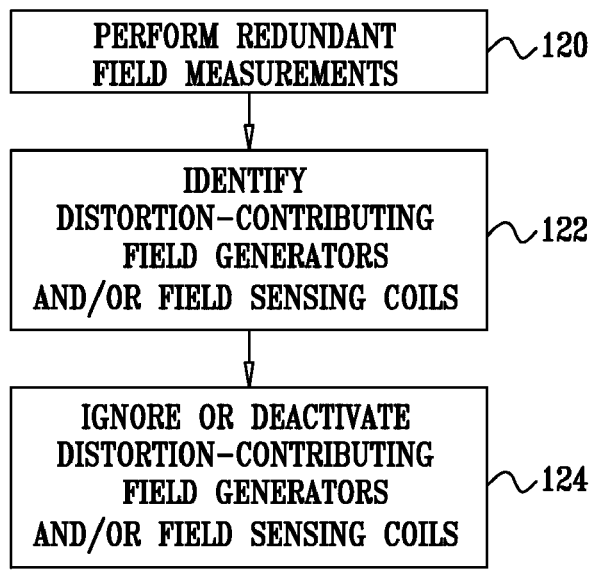

DISTORTION-IMMUNE POSITION TRACKING USING REDUNDANT MEASUREMENTS

This Application is a Continuation Patent Application of U.S. patent application Ser. No. 11/462,733 filed Aug. 7, 2006 now U.S. Pat. No. 8,082,020.

FIELD OF THE INVENTION

The present invention relates generally to magnetic position tracking systems, and particularly to methods and systems for performing accurate position measurements in the presence of field-distorting objects.

BACKGROUND OF THE INVENTION

Various methods and systems are known in the art for tracking the coordinates of objects involved in medical procedures. Some of these systems use magnetic field measurements. For example, U.S. Pat. Nos. 5,391,199 and 5,443,489, whose disclosures are incorporated herein by reference, describe systems in which the coordinates of an intrabody probe are determined using one or more field transducers. Such systems are used for generating location information regarding a medical probe or catheter. A sensor, such as a coil, is placed in the probe and generates signals in response to externally-applied magnetic fields. The magnetic fields are generated by magnetic field transducers, such as radiator coils, fixed to an external reference frame in known, mutually-spaced locations.

Additional methods and systems that relate to magnetic position tracking are also described, for example, in PCT Patent Publication WO 96/05768, U.S. Pat. Nos. 6,690,963, 6,239,724, 6,618,612 and 6,332,089, and U.S. Patent Application Publications 2002/0065455 A1, 2003/0120150 A1 and 2004/0068178 A1, whose disclosures are all incorporated herein by reference. These publications describe methods and systems that track the position of intrabody objects such as cardiac catheters, orthopedic implants and medical tools used in different medical procedures.

It is well known in the art that the presence of metallic, paramagnetic or ferromagnetic objects within the magnetic field of a magnetic position tracking system often distorts the system's measurements. The distortion is sometimes caused by eddy currents that are induced in such objects by the system's magnetic field, as well as by other effects.

Various methods and systems have been described in the art for performing position tracking in the presence of such interference. For example, U.S. Pat. No. 6,147,480, whose disclosure is incorporated herein by reference, describes a method in which the signals induced in the tracked object are first detected in the absence of any articles that could cause parasitic signal components. Baseline phases of the signals are determined. When an article that generates parasitic magnetic fields is introduced into the vicinity of the tracked object, the phase shift of the induced signals due to the parasitic components is detected. The measured phase shifts are used to indicate that the position of the object may be inaccurate. The phase shifts are also used for analyzing the signals so as to remove at least a portion of the parasitic signal components.

SUMMARY OF THE INVENTION

Embodiments of the present invention provide improved methods and systems for performing magnetic position tracking measurements in the presence of metallic, paramagnetic and/or ferromagnetic objects (collectively referred to as field-distorting objects) using redundant measurements.

The system comprises two or more field generators that generate magnetic fields in the vicinity of the tracked object. The magnetic fields are sensed by a position sensor associated with the object and converted to position signals that are used to calculate the position (location and orientation) coordinates of the object. The system performs redundant field strength measurements and exploits the redundant information to reduce the measurement errors caused by the presence of field-distorting objects.

The redundant measurements comprise field strength measurements of magnetic fields generated by different field generators and sensed by field sensors in the position sensor. In an exemplary embodiment described herein, nine field generators and three field sensing coils are used to obtain 27 different field strength measurements. The 27 measurements are used to calculate the six location and orientation coordinates of the tracked object, thus containing a significant amount of redundant information.

In some embodiments, a rotation-invariant coordinate correcting function is applied to the measured field strengths to produce a distortion-corrected location coordinate of the tracked object. As will be shown hereinbelow, the coordinate correcting function exploits the redundant location information so as to reduce the distortion level in the corrected location coordinate.

The coordinate correcting function can be viewed as adjusting the relative contributions of the measured field strengths to the corrected location coordinates responsively to the respective level of the distortion present in each of the measured field strengths. A disclosed clustering process further improves the accuracy of the coordinate correcting function by defining different coordinate correcting functions for different locations.

In some embodiments, the orientation coordinates of the tracked object are calculated following the location calculation. Other disclosed methods improve the accuracy of the orientation calculation in the presence of distortion, and compensate for non-concentricity of the field sensors of the position sensor.

In some embodiments, the redundant field strength measurements are used to identify one or more system elements, such as field generators and/or field sensing elements of the position sensor, which contribute significant distortion. Field measurements associated with these system elements are disregarded when performing the position calculation. In some embodiments, a distortion-contributing element may be deactivated.

There is therefore provided, in accordance with an embodiment of the present invention, a method for tracking a position of an object, including:

using a field sensor associated with the object to measure field strengths of magnetic fields generated by two or more field generators, wherein a measurement of at least one of the field strengths is subject to a distortion;

calculating rotation-invariant location coordinates of the object responsively to the measured field strengths; and determining corrected location coordinates of the object by applying to the rotation-invariant location coordinates a coordinate correcting function so as to adjust a relative contribution of each of the measured field strengths to the corrected location coordinates responsively to the distortion in the measured field strengths.

In some embodiments, the method includes inserting the object into an organ of a patient, and determining the corrected location coordinates of the object includes tracking the position of the object inside the organ.

In an embodiment, the distortion is caused by a field-distorting object subjected to at least some of the magnetic fields, wherein the object comprises at least one material selected from a group consisting of metallic, paramagnetic and ferromagnetic materials.

In a disclosed embodiment, the method includes performing calibration measurements of the magnetic fields at respective known coordinates relative to the two or more field generators, and deriving the coordinate correcting function responsively to the calibration measurements. In another embodiment, the distortion is caused by a movable field-distorting object, and performing the calibration measurements includes performing the measurements at different locations of the field-distorting object. Additionally or alternatively, deriving the coordinate correcting function includes applying a fitting process to a dependence of the calibration measurements on the known coordinates.

In yet another embodiment, applying the coordinate correcting function includes applying a polynomial function having coefficients including exponents of at least some of the rotation-invariant location coordinates.

In still another embodiment, applying the coordinate correcting function includes identifying a distortion-contributing element responsively to the measured field strengths, and producing the coordinate correcting function so as to disregard the measured field strengths that are associated with the distortion-contributing element.

In some embodiments, the field sensor includes one or more field sensing elements, and identifying the distortion-contributing element includes determining that one or more of the field sensing elements and the field generators are contributing to the distortion.

In an embodiment, the method includes calculating angular orientation coordinates of the object.

In another embodiment, the field sensor is used within a working volume associated with the two or more field generators, and determining the corrected location coordinates includes:

dividing the working volume into two or more clusters;
defining for each of the two or more clusters respective two or more cluster coordinate correcting functions; and
applying to each of the rotation-invariant location coordinates one of the cluster coordinate correcting functions responsively to a cluster in which the rotation-invariant location coordinate falls.

Applying the cluster coordinate correcting functions may include applying a weighting function so as to smoothen a transition between neighboring clusters.

In yet another embodiment, the method includes measuring the field strengths using two or more field sensors having non-concentric locations, and compensating for inaccuracies caused by the non-concentric locations in the corrected location coordinates.

There is additionally provided, in accordance with an embodiment of the present invention, a method for tracking a position of an object, including:

using a field sensor associated with the object to perform measurements of field strengths of magnetic fields generated by two or more field generators so as to provide redundant location information, wherein at least some of the field strength measurements are subject to a distortion; and determining location coordinates of the object relative to the two or more field generators by applying to the measurements a coordinate correcting function that exploits the redundant location information so as to reduce an impact of the distortion on the location coordinates.

There is also provided, in accordance with an embodiment of the present invention, a method for tracking a position of an object, including:

using a field sensor, which includes one or more field sensing elements associated with the object, to measure field strengths of magnetic fields generated by two or more field generators, wherein a measurement of at least one of the field strengths is subject to a distortion;

identifying, responsively to the measured field strengths, at least one distortion-contributing system element, which is selected from a group consisting of the one or more field sensing elements and the two or more field generators; and determining the position of the object relative to the two or more field generators responsively to the measured field strengths while disregarding field measurements associated with the distortion-contributing system element.

In an embodiment, the method includes inserting the object into an organ of a patient, and determining the position of the object includes tracking the position of the object inside the organ. In another embodiment, the two or more field generators are associated with the object, and the field sensor is located externally to the organ. In yet another embodiment, identifying the distortion-contributing system element includes accepting an a-priori indication selected from a group consisting of a characteristic direction of the distortion and an identity of the distortion-contributing system element.

In still another embodiment, identifying the distortion-contributing system element includes sensing a presence of the distortion in the field measurements associated with the distortion-contributing system element. In an embodiment, the distortion-contributing system element includes a pair of one of the field sensing elements and one of the field generators. In another embodiment, disregarding the field measurements associated with the distortion-contributing system element includes deactivating the distortion-contributing system element.

There is further provide, in accordance with an embodiment of the present invention, a system for tracking a position of an object, including:

two or more field generators, which are arranged to generate respective magnetic fields in a vicinity of the object;

a field sensor associated with the object, which is arranged to measure field strengths of the magnetic fields, wherein a measurement of at least one of the field strengths is subject to a distortion; and a processor, which is arranged to calculate rotation-invariant location coordinates of the object responsively to the measured field strengths, and to determine corrected location coordinates of the object by applying to the rotation-invariant location coordinates a coordinate correcting function so as to adjust a relative contribution of each of the measured field strengths to the corrected location coordinates responsively to the distortion in the measured field strengths.

There is additionally provided, in accordance with an embodiment of the present invention, a system for tracking a position of an object, including:

two or more field generators, which are arranged to generate respective magnetic fields in a vicinity of the object;

a field sensor associated with the object, which is arranged to perform measurements of field strengths of the magnetic fields so as to provide redundant location information, wherein at least some of the field strength measurements are subject to a distortion; and a processor, which is arranged to determine location coordinates of the object relative to the two or more field generators by applying to the measurements a coordinate correcting function that exploits the redundant location information so as to reduce an impact of the distortion on the location coordinates.

There is also provided, in accordance with an embodiment of the present invention, a system for tracking a position of an object, including:

two or more field generators, which are arranged to generate respective magnetic fields in a vicinity of the object;

a field sensor, which is associated with the object and includes one or more field sensing elements, which is arranged to measure field strengths of the magnetic fields, wherein a measurement of at least one of the field strengths is subject to a distortion; and a processor, which is arranged to identify responsively to the measured field strengths a distortion-contributing system element, which is selected from a group consisting of the one or more field sensing elements and the two or more field generators, and to determine the position of the object relative to the two or more field generators while disregarding field measurements associated with the distortion-contributing system element.

There is further provided, in accordance with an embodiment of the present invention, a computer software product used in a system for tracking a position of an object, the product including a computer-readable medium, in which program instructions are stored, which instructions, when read by the computer, cause the computer to control two or more field generators so as to generate magnetic fields in a vicinity of the object, to accept measurements of field strengths of the magnetic fields performed by a field sensor associated with the object, wherein a measurement of at least one of the field strengths is subject to a distortion, to calculate rotation-invariant location coordinates of the object responsively to the measured field strengths, and to determine corrected location coordinates of the object by applying to the rotation-invariant location coordinates a coordinate correcting function so as to adjust a relative contribution of each of the measured field strengths to the corrected location coordinates responsively to the distortion in the measured field strengths.

There is also provided, in accordance with an embodiment of the present invention, a computer software product used in a system for tracking a position of an object, the product including a computer-readable medium, in which program instructions are stored, which instructions, when read by the computer, cause the computer to control two or more field generators so as to generate magnetic fields in a vicinity of the object, to accept measurements of field strengths of the magnetic fields performed by a field sensor associated with the object, the measurements including redundant location information, wherein at least some of the measurements are subject to a distortion, and to determine location coordinates of the object relative to the two or more field generators by applying to the measurements a coordinate correcting function that exploits the redundant location information so as to reduce an impact of the distortion on the location coordinates.

There is additionally provided, in accordance with an embodiment of the present invention, a computer software product used in a system for tracking a position of an object, the product including a computer-readable medium, in which program instructions are stored, which instructions, when read by the computer, cause the computer to control two or more field generators so as to generate magnetic fields in a vicinity of the object, to accept measurements of field strengths of the magnetic fields performed by a field sensor, which is associated with the object and includes one or more field sensing elements, wherein a measurement of at least one of the field strengths is subject to a distortion, to identify responsively to the measured field strengths a distortion-contributing system element, which is selected from a group consisting of the two or more field generators and the one or more field sensing elements, and to determine the position of the object relative to the two or more field generators while disregarding field measurements associated with the distortion-contributing system element.

The present invention will be more fully understood from the following detailed description of the embodiments thereof, taken together with the drawings in which:

BRIEF DESCRIPTION OF THE DRAWINGS

FIG. 4 is a flow chart that schematically illustrates a method for position tracking in the presence of field distortion, in accordance with an embodiment of the present invention; and FIG. 5 is a flow chart that schematically illustrates a method for position tracking in the presence of field distortion, in accordance with another embodiment of the present invention.

DETAILED DESCRIPTION OF EMBODIMENTS

System Description

Figure 1:
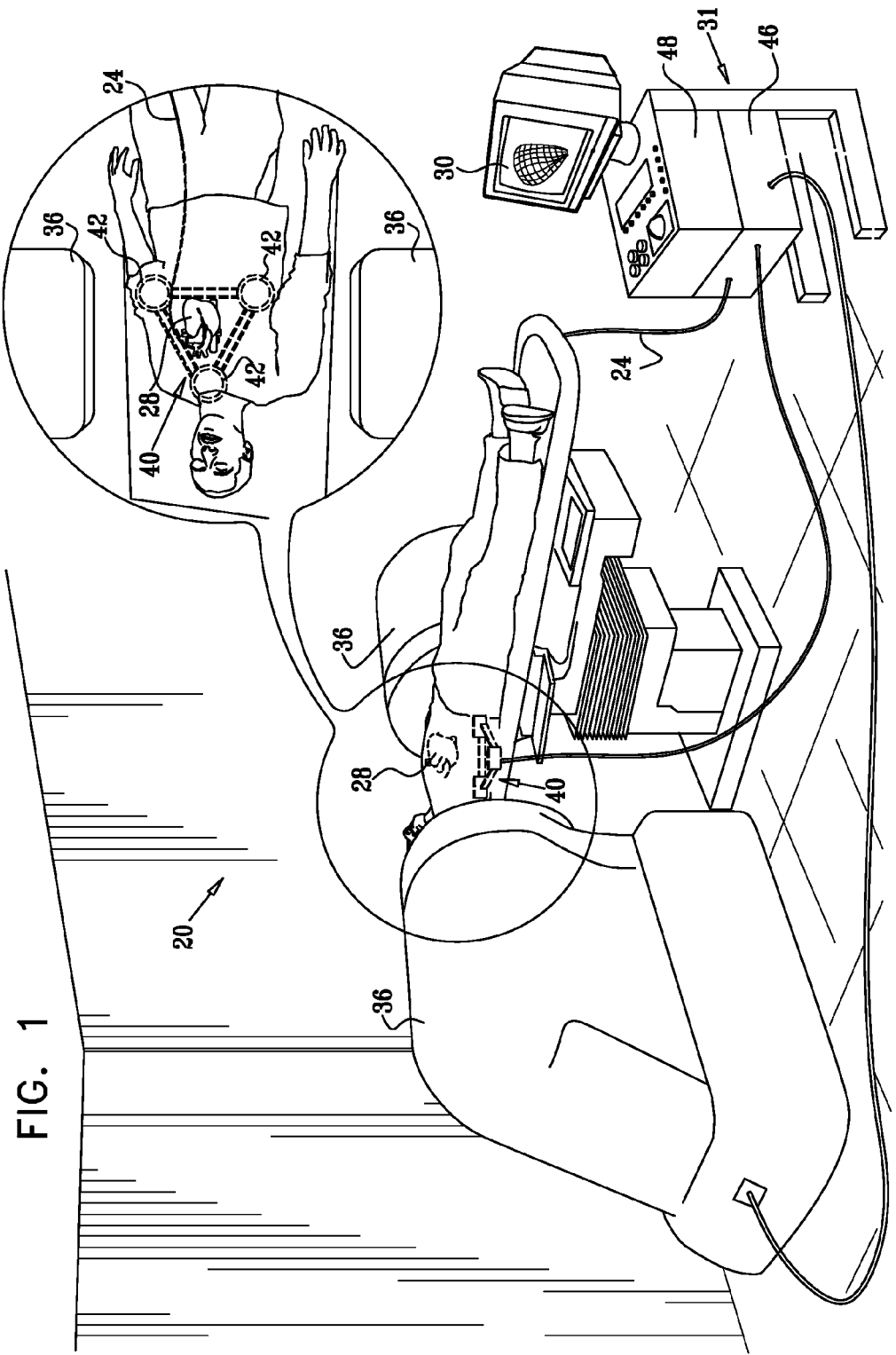
FIG. 1 is a schematic, pictorial illustration of a system for position tracking and steering of intrabody objects, in accordance with an embodiment of the present invention.

FIG. 1 is a schematic, pictorial illustration of a system 20 for position tracking and steering of intrabody objects, in accordance with an embodiment of the present invention. System 20 tracks and steers an intrabody object, such as a cardiac catheter 24, which is inserted into an organ, such as a heart 28 of a patient. System 20 also measures, tracks and displays the position (i.e., the location and orientation) of catheter 24. In some embodiments, the catheter position is registered with a three-dimensional model of the heart or parts thereof. The catheter position with respect to the heart is displayed to a physician on a display 30. The physician uses an operator console 31 to steer the catheter and to view its position during the medical procedure.

System 20 can be used for performing a variety of intracardiac surgical and diagnostic procedures in which navigation and steering of the catheter is performed automatically or semi-automatically by the system, and not manually by the physician. The catheter steering functions of system 20 can be implemented, for example, by using the Niobe® magnetic navigation system produced by Stereotaxis, Inc. (St. Louis, Mo.). Details regarding this system are available at www.stereotaxis.com. Methods for magnetic catheter navigation are also described, for example, in U.S. Pat. Nos. 5,654,864 and 6,755,816, whose disclosures are incorporated herein by reference.

System 20 positions, orients and steers catheter 24 by applying a magnetic field, referred to herein as a steering field, in a working volume that includes the catheter. An internal magnet is fitted into the distal tip of catheter 24. (Catheter 24 is shown in detail in FIG. 3 below.) The steering field steers (i.e., rotates and moves) the internal magnet, thus steering the distal tip of catheter 24.

The steering field is generated by a pair of external magnets 36, typically positioned on either side of the patient. In some embodiments, magnets 36 comprise electro-magnets that generate the steering field responsively to suitable steering control signals generated by console 31. In some embodiments, the steering field is rotated or otherwise controlled by physically moving (e.g., rotating) external magnets 36 or parts thereof. The difficulties that arise from having large metallic objects whose position may very over time, such as magnets 36, in close proximity to the working volume will be discussed hereinbelow.

System 20 measures and tracks the location and orientation of catheter 24 during the medical procedure. For this purpose, the system comprises a location pad 40.

Figure 2:
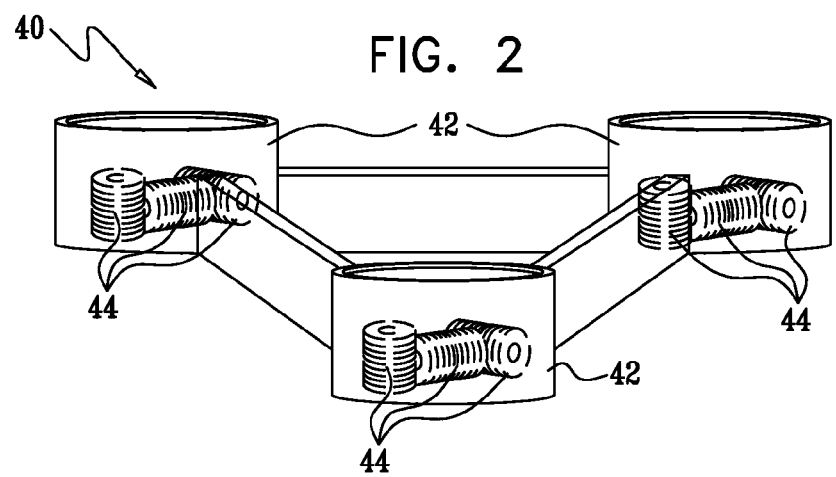
FIG. 2 is a schematic, pictorial illustration of a location pad, in accordance with an embodiment of the present invention.

FIG. 2 is a schematic, pictorial illustration of location pad 40, in accordance with an embodiment of the present invention. Location pad 40 comprises field generators, such as field generating coils 44. Coils 44 are positioned at fixed, known locations and orientations in the vicinity of the working volume. In the exemplary configuration of FIGS. 1 and 2, location pad 40 is placed horizontally under the bed on which the patient lies. Pad 40 in this example has a triangular shape and comprises three tri-coils 42. Each tri-coil 42 comprises three field generating coils 44. Thus, in the present example, location pad 40 comprises a total of nine field generating coils. The three coils 44 in each tri-coil 42 are oriented in mutually-orthogonal planes. In alternative embodiments, location pad 40 may comprise any number of field generators arranged in any suitable geometrical configuration.

Referring to FIG. 1, console 31 comprises a signal generator 46, which generates drive signals that drive coils 44. In the embodiments shown in FIGS. 1 and 2, nine drive signals are generated. Each coil 44 generates a magnetic field, referred to herein as a tracking field, responsively to the respective drive signal driving it. The tracking fields comprise alternating current (AC) fields. Typically, the frequencies of the drive signals generated by signal generator 46 (and consequently the frequencies of the respective tracking fields) are in the range of several hundred Hz to several KHz, although other frequency ranges can be used as well.

A position sensor fitted into the distal tip of catheter 24 senses the tracking fields generated by coils and produces respective position signals, which are indicative of the location and orientation of the sensor with respect to the field generating coils. The position signals are sent to console 31, typically along a cable running through catheter 24 to the console. Console 31 comprises a tracking processor 48, which calculates the location and orientation of catheter 24 responsively to the position signals. Processor 48 displays the location and orientation of the catheter, typically expressed as a six-dimensional coordinate, to the physician using display 30.

Processor 48 also controls and manages the operation of signal generator 46. In some embodiments, field generating coils 44 are driven by drive signals having different frequencies, so as to differentiate between their magnetic fields. Alternatively, the field generating coils can be driven sequentially so that the position sensor measures the tracking field originating from a single coil 44 at any given time. In these embodiments, processor 48 alternates the operation of each coil 44 and associates the position signals received from the catheter with the appropriate field generating coil.

Typically, tracking processor 48 is implemented using a general-purpose computer, which is programmed in software to carry out the functions described herein. The software may be downloaded to the computer in electronic form, over a network, for example, or it may alternatively be supplied to the computer on tangible media, such as CD-ROM. The tracking processor may be integrated with other computing functions of console 31.

Figure 3:
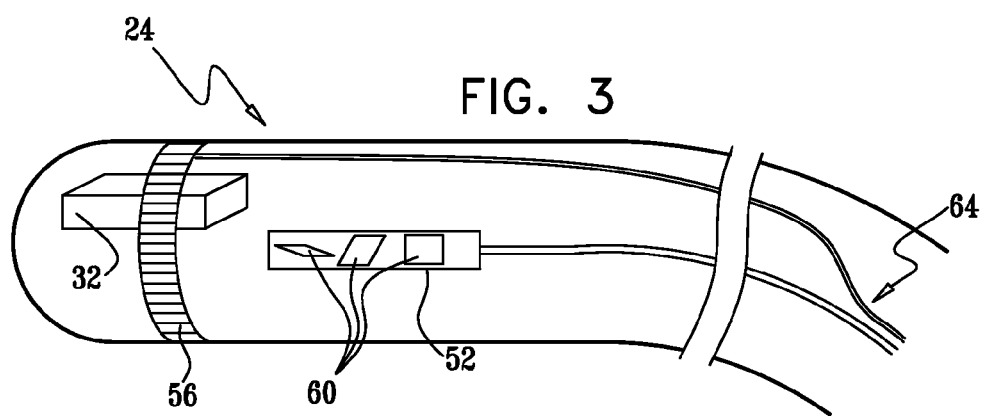
FIG. 3 is a schematic, pictorial illustration of a catheter, in accordance with an embodiment of the present invention.

FIG. 3 is a schematic, pictorial illustration of the distal tip of catheter 24, in accordance with an embodiment of the present invention. Catheter 24 comprises an internal magnet 32 and a position sensor 52, as described above. Catheter 24 may also comprise one or more electrodes 56, such as ablation electrodes and electrodes for sensing local electrical potentials. Position sensor 52 comprises field sensing elements, such as field sensing coils 60. In some embodiments, position sensor 52 comprises three field sensing coils 60 oriented in three mutually-orthogonal planes. Each coil 60 senses one of the three orthogonal components of the AC tracking field and produces a respective position signal responsively to the sensed component. Sensor 52 and electrodes 56 are typically connected to console 31 via cables 64 running through the catheter.

It is well known in the art that metallic, paramagnetic and ferromagnetic objects (collectively referred to herein as field-distorting objects) placed in an AC magnetic field cause distortion of the field in their vicinity. For example, when a metallic object is subjected to an AC magnetic field, eddy currents are induced in the object, which in turn produce parasitic magnetic fields that distort the AC magnetic field. Ferromagnetic objects distort the magnetic field by attracting and changing the density and orientation of the field lines.

In the context of a magnetic position tracking system, when a field-distorting object is present in the vicinity of position sensor 52, the tracking field sensed by sensor 52 is distorted, causing erroneous position measurements. The severity of the distortion generally depends on the amount of field-distorting material present, to its proximity to the position sensor and to the field generating coils, and/or to the angle in which the tracking field impinges on the field-distorting object. In the system of FIG. 1, for example, external magnets 36 typically contain a large mass of field-distorting material and are located in close proximity to the working volume. As such, external magnets 36 may cause a significant distortion of the tracking field sensed by the position sensor.

The methods and systems described hereinbelow are mainly concerned with performing accurate position tracking measurements in the presence of severe distortion of the tracking magnetic field. The catheter steering system of FIG. 1 is described purely as an exemplary application, in which objects located in or near the working volume of the position tracking system cause a severe, time varying distortion of the tracking field. However, embodiments of the present invention are in no way limited to magnetic steering applications. The methods and systems described herein can be used in any other suitable position tracking application for reducing such distortion effects. For example, the methods and systems described herein can be used to reduce field distortion effects caused by object such as C-arm fluoroscopes and magnetic resonance imaging (MRI) equipment.

In alternative embodiments, system 20 can be used to track various types of intrabody objects, such as catheters, endoscopes and orthopedic implants, as well as for tracking position sensors coupled to medical and surgical tools and instruments.

Distortion Reduction Method Using Redundant Measurement Information

As noted above, system 20 comprises nine field generating coils 44 that generate nine respective tracking fields. Each of these fields is sensed by three field sensing coils 60. Thus, the system performs a total of 27 field projection measurements in order to calculate the six location and orientation coordinates of catheter 24. It is evident that the 27 measurements contain a significant amount of redundant information. This redundant information can be used to improve the immunity of the system to distortions caused by field-distorting objects, such as external magnets 36.

The 27 field measurements can be viewed as vectors in a 27-dimensional vector space. Each dimension of this vector space corresponds to a pair of {field generating coil 44, field sensing coil 60}. Because of the redundancy in the measurements, it is often possible to determine a lower dimensionality sub-space of this vector space that is invariant or nearly invariant to the field distortions. The position tracking method described in FIG. 4 below uses the redundant information present in the field measurements to improve the accuracy of the position measurements in the presence of such field distortions.

In principle, the method first calculates three location vectors that define the location of position sensor 52 relative to the three tri-coils 42, respectively. These location vectors are invariant to the angular orientation of the position sensor and are referred to as rotation invariants. The location vectors are orientation-invariant since, as will be shown below, they are calculated based on measured field intensity and not based on the projection of the field strength onto the field sensing coils.

The location vectors (rotation invariants) are corrected by coordinate correcting functions, which exploit the redundant measurement information to improve field distortion immunity. The orientation coordinates of the position sensor are then calculated to complete the six-dimensional location and orientation coordinate of the sensor. In some embodiments, the method of FIG. 4 also comprises calibration and clustering steps, as well as a process for compensating for the non-concentricity of coils 60 of position sensor 52.

Although the method of FIG. 4 below refers to a location pad comprising nine field generating coils arranged in three mutually-orthogonal groups in tri-coils 42 and to a position sensor comprising three mutually-orthogonal field sensing coils, this configuration is an exemplary configuration chosen purely for the sake of conceptual clarity. In alternative embodiments, location pad 40 and position sensor 52 may comprise any number of coils 44 and coils 60 arranged in any suitable geometrical configuration.

FIG. 4 is a flow chart that schematically illustrates a method for position tracking in the presence of field distortion, in accordance with an embodiment of the present invention. The method begins by mapping and calibrating the tracking fields generated by location pad 40, at a calibration step 100.

Typically, the calibration process of step 100 is performed during the production of location pad 40, and the calibration results are stored in a suitable memory device coupled to the location pad. Calibration setups that can be used for this purpose and some associated calibration procedures are described, for example, in U.S. Pat. No. 6,335,617, whose disclosure is incorporated herein by reference.

In the calibration process, a calibrating sensor similar to position sensor 52 is scanned through multiple locations in the three-dimensional working volume around pad 40. At each location of the calibrating sensor, each of the nine field generating coils 44 in pad 40 is driven to generate a respective tracking field, and the three field sensing coils 60 of the calibrating sensor measure this tracking field. The sensed field strengths associated with each location are recorded.

In some embodiments, the calibration process comprises performing multiple field measurements at each location of the calibrating sensor. Typically, some of these measurements comprise free-space measurements (i.e., measurements taken when the working volume and its vicinity are free of field-distorting objects). Other measurements are taken in the presence of field-distorting objects, in the same positions they are expected to have during the system operation. For example, when the field-distorting objects comprise external magnets 36 that are physically moved to steer catheter 24, field measurements are performed while the magnets are moved through their entire expected motion range. Other field-distorting objects that may be included in the calibration include, for example, a fluoroscope used to irradiate the patient, as well as the bed the patient lies on.

The calibration setup performs the field measurements and records the measurement results along with the associated known locations of the calibrating sensor. In some embodiments, the calibration procedure is carried out by a robot or other automatic calibration setup that moves the calibration sensor across the working volume around pad 40.

In some embodiments, every pad 40 being produced is calibrated using the calibration procedure described herein. Alternatively, such as when the production process of pads 40 is sufficiently repeatable, the full calibration procedure may be performed only on a single location pad or a sample of pads and the results used to calibrate the remaining pads. Further alternatively, a sample of pads may be subjected to the full calibration procedure. For the remaining pads, only differential results, indicating the field strength differences between free-space measurements and distorted measurements, are recorded.

In some cases, the material composition, mechanical structure and/or location of the field-distorting objects is known. In such cases, the interference caused by these objects can be modeled, and the model used as part of the calibration measurements. In some cases, when multiple field-distorting objects are present, calibration measurements may be performed for each object separately. The individual calibration measurements can then be combined. Further additionally or alternatively, any other suitable method of obtaining a set of calibration measurements can be used.

The multiple field projection measurements, each associated with a known location of the calibrating sensor, are used to derive three rotation-invariant coordinate correcting functions. The correcting functions will later be applied during normal system operation. The functions accept as input a set of raw field measurements, as measured by position sensor 52. These raw measurements may be distorted due to the presence of field-distorting objects. The three functions produce three respective corrected location coordinates of position sensor 52 with respect to location pad 40. In some embodiments, the correcting functions compensate for distortion from field-distorting objects, as well as for errors due to the fact that the tracking fields generated by coils 44 deviate from ideal dipole fields. Modeling the tracking fields as dipole fields is, however, not mandatory.

In some embodiments, the coordinate correcting functions are determined using a fitting process. The fitting process determines the functions that best fit the location coordinates measured during calibration step 100 above to the known location coordinates of the calibrating sensor. Any suitable fitting method known in the art can be used for this purpose, such as, for example, polynomial regression methods.

Thus, the fitting process effectively causes the coordinate correcting functions to adjust the relative contribution of each raw location coordinate to the corrected location coordinate responsively to the level of distortion contained in the raw measurements. Raw location coordinates having low distortion content are likely to be emphasized, or given more weight, by the fitting process. Raw location coordinates having high distortion content are likely to be given less weight, or even ignored.

The coordinate correcting functions can thus be viewed as transforming the raw field measurements into a sub-space that is as invariant as possible to the distortion. Since the fitting process takes into consideration the bulk of calibration measurements, the sub-space is invariant to the distortion caused in different field-distorting object geometries.

In some embodiments, the coordinate correcting function can disregard field measurements associated with one or more distortion-contributing system elements that contribute a significant amount of distortion to the calculation. Distortion-contributing elements may comprise field generating coils 44, field sensing coils and/or pairs of {coil 44, coil 60}. In these embodiments, the function may ignore the measurements related to the distortion-contributing elements, for example by setting appropriate coefficients of the coordinate correcting function to zero or otherwise shaping the function to be insensitive to these elements. In some embodiments, the distortion-contributing elements can be switched off or otherwise deactivated.

The raw location coordinates are expressed as three vectors denoted $r_{tc}$, wherein tc=1 ... 3 indicates an index of the tri-coil 42 used in the measurement. Vector $r_{tc}$ comprises three location coordinates $\{x_{tc}, y_{tc}, z_{tc}\}$ indicating the location coordinates of the position sensor, as calculated responsively to the tracking fields generated by tri-coil tc. By convention, $r_{tc}$ is expressed relative to a reference frame of location pad 40. An exemplary mathematical procedure for calculating $r_{tc}$ based on the measured field strengths, assuming an ideal dipole field, is given in step 102 further below.

In some embodiments, the three coordinate correcting functions comprise polynomial functions. In the description that follows, each function comprises a third-order polynomial of the location coordinates that does not contain any cross-terms (i.e., the polynomial may contain $x$, $x^2$, $x^3$, $y$, $y^2$, $y^3$, $z$, $z^2$ and $z^3$ terms but not, for example, $xy^2$, $xyz$ or $y^2z$ terms). The input to the coordinate correcting functions can thus be expressed as a 28-dimensional vector denoted In, which is defined as In={1, $r_1$, $r_2$, $r_3$, $r_1^2$, $r_2^2$, $r_3^2$, $r_1^3$, $r_2^3$, $r_3^3$}={1, $x_1$, $y_1$, $z_1$, $x_2$, $y_2$, $z_2$, $x_3$, $y_3$, $z_3$, $x_1^2$, $y_1^2$, $z_1^2$, $x_2^2$, $y_2^2$, $z_2^2$, $x_3^2$, $y_3^2$, $z_3^2$, $x_1^3$, $y_1^3$, $z_1^3$, $x_2^3$, $y_2^3$, $z_2^3$, $x_3^3$, $y_3^3$, $z_3^3$}, wherein the first "1" term serves as an offset. The three coordinate correcting functions have the form $$x_{cor} = \sum_{i=1}^{28} \alpha_i In_i$$

$$y_{cor} = \sum_{i=1}^{28} \beta_i In_i$$

$$z_{cor} = \sum_{i=1}^{28} \gamma_i In_i$$

[1]

wherein $x_{cor}$, $y_{cor}$ and $z_{cor}$ respectively denote the distortion-corrected x, y and z location coordinates of position sensor 52, with respect to location pad 40. Coefficients $\alpha_1 \ldots \alpha_{28}$, $\beta_1 \ldots \beta_{28}$ and $\gamma_1 \ldots \gamma_{28}$ denote the coefficients of the polynomial functions. In the present example, The fitting process described above comprises fitting the values of the polynomial coefficients.

The three sets of coefficients can be arranged in a coefficient matrix denoted $L_{coeff}$, defined as $$L_{coeff} = \begin{bmatrix} \alpha_1 & \beta_1 & \gamma_1 \\ \alpha_2 & \beta_2 & \gamma_2 \\ \ldots & \ldots & \ldots \\ \alpha_{28} & \beta_{28} & \gamma_{28} \end{bmatrix}$$

[2]

Using this representation, the corrected location coordinates of the position sensor are given by $$r_{cor} = \{x_{cor}, y_{cor}, z_{cor}\} = In \cdot L_{coeff}$$

[3]

In order to further clarify the effectiveness of the coordinate correcting functions, consider a particular location of the calibration sensor. During the calibration process of step 100, multiple field strength measurements are performed at this particular location, both in free space and in the presence of distortion from different field-distorting objects, as expected to occur during the normal operation of the system. The coordinate correcting functions replace these multiple measurements with a single corrected value, which best fits the known location coordinate of the calibrating sensor.

The coordinate correcting functions effectively exploit the redundant information contained in the 27 raw location measurements to improve distortion immunity. For example, since the intensity of a magnetic field decays rapidly with distance (proportionally to $1/r^3$), measurements performed using a tri-coil 42 that is further away from the field-distorting object will typically produce measurements containing less distortion. In such cases, the fitting process will typically give a higher weight to the measurements associated with this lower distortion tri-coil when calculating coefficients $\alpha_i$, $\beta_i$ and $\gamma_i$ of the coordinate correcting functions.

As another example, in many cases, the field distortion is highly sensitive to the angle in which of the magnetic field impinges on the field-distorting object. Since the three field generating coils 44 in each tri-coil 42 are mutually-orthogonal, there will typically exist at least one coil 44 whose tracking field generates little or no distortion. Again, the fitting process used to calculate coefficients $\alpha_i$, $\beta_i$ and $\gamma_i$ will typically give a higher weight to the measurements associated with this lower distortion coil 44.

In summary, calibration step 100 comprises mapping the working volume around location pad 40, followed by derivation of coordinate correcting functions that will later on translate measured raw location coordinates to distortion-corrected location coordinates of position sensor 52.

Steps 102-110 below are carried out by tracking processor 48 during the normal operation of system 20, whenever a position tracking measurement is desired. Processor 48 calculates the rotation-invariant location coordinates $r_{tc}$ (also referred to as the raw location coordinates), at an invariant calculation step 102. As noted above, the calculation that follows assumes that the tracking fields generated by coils 44 are ideal dipole fields.

For each tri-coil 42 having an index tc=1 ... 3, processor 48 calculates a field intensity matrix denoted MtM, which is defined as $$MtM = (U_{tc} \cdot M_{tc})^t \cdot (U_{tc} \cdot M_{tc})$$

[4]

wherein $U_{tc}$ is a 3-by-3 matrix containing the field strengths of the tracking fields generated by the three field generating coils 44 of tri-coil tc, as measured by the three field sensing coils 60 of position sensor 52. Each matrix element $(U_{tc})_{ij}$ denotes the field strength generated by the $j^{th}$ field generating coil 44 in tri-coil tc, as sensed by the ith field sensing coil 60 of sensor 52. Matrix $M_{tc}$ is a 3-by-3 matrix comprising the inverse of the magnetic moment matrix of tri-coil tc. The operator $(\ )^t$ denotes matrix transposition.

Processor 48 now calculates |r|, which denotes the radius-vector, or magnitude, of location vector $r_{tc}$. |r| is given by $$\|r\| = \text{Trace}(\sqrt[6]{MtM/6}).$$

The direction of vector $r_{tc}$ is approximated by the direction of the eigenvector of matrix MtM corresponding to the largest eigenvalue. In order to determine this eigenvector, processor 48 applies a singular value decomposition (SVD) process, as is known in the art, to matrix MtM:

$$[u,w,u^t] = \text{SVD}(MtM) \qquad [5]$$

wherein u denotes the eigenvectors and w denotes the eigenvalues of matrix MtM.

Let u(1) denote the eigenvector corresponding to the largest eigenvalue. In order to resolve ambiguity, the z-axis component of u(1) (by convention, the third component of the eigenvector) is forced to be positive by selecting the mirror image of the vector u(1) if necessary. In other words, IF u(1)·{0,0,1}<0 THEN u(1)=−u(1). Finally, the raw location coordinate vector $r_{tc}$ is estimated by $$r_{tc} = \|r\| \cdot u(1) + c_{tc} \qquad [6]$$

wherein $c_{tc}$ denotes the location coordinate vector of tri-coil tc in the coordinate system of location pad 40.

Tracking processor 48 typically repeats the process of step 102 for all three tri-coils 42 of pad 40. The output of step 102 is three vectors $r_{tc}$, tc=1 . . . 3, giving the raw location coordinates of position sensor 52 relative to tri-coils 42. As noted above, the raw location coordinates are uncorrected and may contain distortion caused by field-distorting objects.

Processor 48 now calculates the distortion-corrected location coordinates of sensor 52, at a corrected coordinate calculation step 104. Processor 48 uses the coordinate correcting functions calculated at calibration step 100 above for this purpose. In the exemplary embodiment described above, in which the functions comprise third-order polynomials, the three coordinate correcting functions are expressed in terms of matrix $L_{coeff}$ as defined in equation [2] above. In this embodiment, vector $r_{cor}$ denoting the distortion-corrected location coordinates of sensor 52 is given by $$r_{cor} = \text{In} \cdot L_{coeff} \qquad [7]$$

wherein In denotes the input vector of raw location coordinates and their exponents, as described above. In alternative embodiments, vector $r_{cor}$ is calculated by applying the coordinate correction functions to the measured raw location coordinates.

In some embodiments, tracking processor 48 applies a clustering process to the location measurements, at a clustering step 106. The accuracy of the coordinate correcting functions can often be improved by dividing the working volume into two or more sub-volumes, referred to as clusters, and defining different coordinate correcting functions for each cluster.

Let N denote the number of clusters. In embodiments in which the coordinate correcting functions are expressed in terms of matrix $L_{coeff}$ for example, processor 48 calculates for each cluster c (c=1 . . . N) a cluster coefficient matrix denoted $L_{coeff-c}$ at calibration step 100 above. At step 104 above, processor 48 determines the cluster to which each raw location coordinate measurement belongs, and applies the appropriate cluster coefficient matrix to produce the distortion-corrected location coordinates.

In some embodiments, the transitions between neighboring clusters are smoothed using a weighting function. In these embodiments, a prototype coordinate denoted $p_c$ is defined for each cluster c, typically located in the center of the cluster. Processor 48 calculates a weighted corrected coordinate denoted $r_w$ by summing the corrected location coordinates calculated using the coordinate correcting functions of each cluster, weighted by the distance of the raw coordinate r from the prototype coordinate $p_c$ of the cluster:

$$r_w = \sum_{i=1}^{N} f(r - p_c) \cdot \text{In} \cdot L_{coeff-c} \qquad [8]$$

The weighting function $f(r-p_c)$ is defined as $$f(r - p_c) = \frac{1}{1 + \left(\frac{r - p_c}{a}\right)^{2t}} \qquad [9]$$

wherein a and t are constants used to appropriately shape the weighting function.

In some embodiments, processor 48 verifies that the raw location coordinate being processed is indeed located inside the working volume mapped at step 100 above. This validity check is sometimes desirable in order to ensure that the coordinate correcting functions being used are indeed valid for the coordinate in question. In some embodiments, if the raw location coordinate is found to be outside the mapped working volume, processor 48 notifies the physician of the situation, such as by displaying the coordinate using a different color or icon or by presenting an alert message. In some embodiments, the raw coordinate is displayed without applying correction. Alternatively, the measurement may be discarded.

For example, in some embodiments, processor 48 produces a validity matrix denoted V during calibration step 100. Matrix V comprises a three-dimensional bit matrix, in which each bit corresponds to a three-dimensional voxel (i.e., a unit volume, the three-dimensional equivalent of a pixel) in the working volume having a resolution denoted d. Each bit of matrix V is set if the corresponding voxel coordinate is within the mapped working volume, otherwise the bit is reset.

In order to preserve memory space, matrix V can be represented as a two-dimensional array of 32-bit words. The two indices of the array correspond to the x and y coordinates of the voxel, and each bit in the indexed 32-bit word corresponds to the z-axis coordinate of the voxel. The following pseudo-code shows an exemplary method for indexing matrix V in order to verify whether a coordinate {x,y,z} is located within the valid working volume:

{xInx,yInx,zInx}=round[({x,y,z}−{$x_0,y_0,z_0$})/d];

xInx=Max[MinX,Min[MaxX,xInx]];

yInx=Max[MinY,Min[MaxY,xIny]];

zInx=Max[MinZ,Min[MaxZ,xInz]];

valid=bitSet[V(xInx,yInx),zInx];

wherein round[x] denotes the integer closest to x, and $\{x_0, y_0, z_0\}$ denote the corner coordinates of the mapped working volume. $\{xInx, yInx, zInx\}$ denote indices to matrix V. MinX, MaxX, MinY, MaxY, MinZ, MaxZ denote range limits of the x, y and z coordinates, respectively. If the extracted valid bit is set, processor 48 concludes that coordinate $\{x,y,z\}$ is located within the mapped working volume, and vice versa.

In some embodiments, two or more validity matrices may be defined. For example, the boundary, or outskirts, of the working volume may be mapped separately and defined using a second validity matrix.

At this stage, processor 48 has calculated a distortion-corrected location coordinate of position sensor 52, typically expressed as a three-dimensional coordinate. In order to obtain the complete six-dimensional coordinate of the position sensor, processor 48 now calculates the angular orientation coordinates of the position sensor, at an orientation calculation step 108.

In some embodiments, the orientation coordinates are calculated using the relation $$M_{tc} = R \cdot B_{tc}$$

wherein $M_{tc}$ denotes the inverse moment matrix described above, R denotes a rotation matrix representing the angular orientation of sensor 52 with respect to the coordinate system of location pad 40, and $B_{tc}$ denotes the measured magnetic field at coils 60 of sensor 52.

Matrix R can be estimated by $$R = M \cdot B^t \cdot (B \cdot B^t)^{-1} \quad [10]$$

wherein $$M = \begin{bmatrix} M_1 \\ M_2 \\ M_3 \end{bmatrix} \text{ and } B = \begin{bmatrix} B_1 \\ B_2 \\ B_3 \end{bmatrix}.$$

The measurements of $B_{tc}$ may contain distortion from field-distorting objects, which may in turn affect the estimation accuracy of matrix R. The estimation accuracy may be improved by applying a symmetrical decomposition process to R. For example, let $R^2 = R^t \cdot R$. Processor 48 applies a SVD process to $R^2$:

$$V \cdot \begin{bmatrix} u_1^2 & 0 & 0 \\ 0 & u_2^2 & 0 \\ 0 & 0 & u_3^2 \end{bmatrix} \cdot V^t = SVD[R^2] \quad [11]$$

wherein $u_1^2$, $u_2^2$ and $u_3^2$ denote the eigenvalues of $R^2$. Define S as:

$$S = (-R^2 + (u_1 \cdot (u_1 + u_2) + u_2 \cdot (u_2 + u_3) + u_3 \cdot (u_3 + u_1)) \cdot R^2 + \quad [12]$$
$$u_1 \cdot u_2 \cdot u_3 \cdot (u_1 + u_2 + u_3)) \begin{bmatrix} 1 & 0 & 0 \\ 0 & 1 & 0 \\ 0 & 0 & 1 \end{bmatrix}$$

Processor 48 calculates an improved accuracy rotation matrix denoted $\tilde{R}$, which is given by:

$$\tilde{R} = R \cdot S^{-1} \quad [13]$$

Having calculated the distortion-corrected location and orientation coordinates, processor 48 now has the full six-dimensional coordinates of position sensor 52.

Until now it was assumed that field sensing coils 60 of position sensor 52 are concentric, i.e., have identical location coordinates. In some cases, however, sensor 52 is constructed so that coils 60 are not concentric. This non-concentricity introduces an additional inaccuracy into the distortion-corrected coordinates. In some embodiments, tracking processor 48 compensates for the inaccuracies caused by the non-concentricity of the field sensing coils, at a non-concentricity compensation step 110.

For example, processor 48 may apply an iterative compensation process to compensate for such inaccuracies. Consider the tracking field denoted $ME_{tc,co}$, which is generated by a coil co of tri-coil tc and measured by a non-concentric position sensor 52. Let vector $\vec{r}$ denote the location coordinate of one of coils 60 of the sensor, used as a reference coordinate, with respect to tri-coil tc. Let $\vec{r}_{c1}$ and $\vec{r}_{c2}$ denote two vectors defining the location offsets of the other two field sensing coils with respect to the first (reference) coil. The tracking field generated by coil co of tri-coil tc in sensor 52 is given by:

$$ME_{tc,co} = \tilde{R} \cdot \begin{bmatrix} B_{tc,co}(\vec{r} + R^t \cdot \vec{r}_{c1})(1) \\ B_{tc,co}(\vec{r})(2) \\ B_{tc,co}(\vec{r} + R^t \cdot \vec{r}_{c2})(3) \end{bmatrix} \quad [14]$$

wherein the second line of the field vector corresponds to the reference coil. $\tilde{R}$ denotes the improved accuracy rotation matrix defined by equation [13] above.

Processor 48 improves the estimation of $ME_{tc,co}$ by iteratively repeating steps 104-108 above. At each iteration step i+1, the measured field is given by $$ME_{tc,co}^{i+1} = ME_{tc,co} + \tilde{R}^i \cdot \begin{bmatrix} B_{tc,co}^i(\vec{r} + (R^t)^i \cdot \vec{r}_{c1})(1) - B_{tc,co}^i(\vec{r})(1) \\ 0 \\ B_{tc,co}^i(\vec{r} + (R^t)^i \cdot \vec{r}_{c2})(3) - B_{tc,co}^i(\vec{r})(3) \end{bmatrix} \quad [15]$$

In some embodiments, processor 48 performs a predetermined number of iteration steps. Alternatively, a convergence threshold th is defined, and the iterative process is repeated until $$(B_{tc,co}^i(\vec{r} + (r^t)^i \cdot \vec{r}_{c1})(1) - B_{tc,co}^i(\vec{r})(1))^2 + (B_{tc,co}^i( \vec{r} + (R^t)^i \cdot \vec{r}_{c2})(3) - B_{tc,co}^i(\vec{r})(3))^2 < th \quad [16]$$

Distortion Reduction Method Using Directional Selection

As noted above, in some cases the distortion introduced into a particular field strength measurement is highly dependent on the mutual location and/or orientation of the field generating coil used, the field sensing coil used and the field-distorting object causing the distortion. Therefore, when redundant field measurements are performed using multiple field generating coils 44 and field sensing coils 60 having different locations and orientations, it is often possible to identify one or more coil 44 and/or coil 60 that are dominant contributors of distortion. Discarding the measurements related to these distortion-contributing system elements may significantly reduce the total amount of distortion in the position calculation.

FIG. 5 is a flow chart that schematically illustrates a method for position tracking in the presence of field distortion, based on recognizing and eliminating distortion-contributing elements, in accordance with another embodiment of the present invention. The method of FIG. 5 refers to a single position tracking calculation, at a single position of catheter 24 in the patient's body. This method can be applied, of course, at multiple positions distributed throughout the working volume of a position tracking system.

The method begins with system 20 performing redundant field measurements, at a measurement step 120. Typically, multiple field strength measurements are taken using different pairs of {field generating coil 44, field sensing coil 60}. As noted above, the exemplary system configuration of FIGS. 1 and 2 comprises a total of 27 coil pairs, resulting in a maximum number of 27 redundant field measurements.

Tracking processor 48 now identifies one or more distortion-contributing measurements out of the redundant field measurements, at an identification step 122. The distortion-contributing measurements are characterized by a high level of distortion. In some embodiments, processor 48 may automatically detect and quantify the level of distortion in the redundant field measurements. Any suitable method may be used for this purpose, such as, for example, methods described in U.S. Pat. No. 6,147,480 cited above. Using the distortion-contributing measurements, processor 48 identifies one or more distortion-contributing system elements, which may comprise field generating coils 44, field sensing coils 60 and/or pairs of {coil 44, coil 60} that are associated with the distortion-contributing measurements.

Additionally or alternatively, the characteristic direction of the distortion may be indicated to processor a-priori. In some cases, the known direction of distortion indicates to the processor which of coils 44 and/or coils 60 is particularly susceptible to the distortion, and is therefore likely to comprise a distortion-contributing element. Further alternatively, the identity of a particular coil 44, coil 60 and/or pair {coil 44, coil 60} that produces (or is likely to produce) distortion-contributing measurements can be indicated to the processor a-priori.

Tracking processor 48 calculates the position coordinates of position sensor 52 (and of catheter 24) while disregarding the measurements associated with the distortion-contributing elements, at a position calculation step 124. In some embodiments, the measurements associated with a distortion-contributing element are ignored or discarded from the position calculation. Alternatively, a particular distortion-contributing element can be switched off or otherwise deactivated.

Processor 48 may use any suitable position tracking method for calculating the position of sensor 52 (and of catheter 24) in conjunction with the method of FIG. 5, such as the method of FIG. 4 hereinabove, as well as methods described in some of the publications cited above.

In some embodiments, the method shown in FIG. 5 above can be similarly used in system configurations in which the tracking fields are generated by catheter 24 and sensed by externally-located position sensors. In these embodiments, signal generator 46 produces drive signals that drive the field generators in catheter 24 to produce the tracking fields. The external position sensors sense the tracking fields. The sensed fields are then used, in accordance with the appropriate method, to determine a distortion-free position of catheter 24.

Although the embodiments described herein mainly refer to improving the distortion immunity of medical position tracking and steering systems, these methods and systems can be used in additional applications, such as for reducing the distortion caused by the operating room table, fluoroscopy equipment, MRI equipment and/or any other field-distorting object.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art.

The invention claimed is:

1. A method for tracking a position of an object, comprising:
    using a field sensor, which comprises one or more field sensing elements associated with the object, and determining redundant field measurements using the one or more field sensing elements to measure redundant field strengths of magnetic fields generated by two or more field generators so as to provide redundant location information, wherein a measurement of at least one of the field strengths is subject to a distortion;
    identifying, responsively to the measured field strengths, at least one distortion-contributing system element, which is selected from a group consisting of the one or more field sensing elements and of the two or more field generators; and
    determining location coordinates of the object relative to the two or more field generators responsively to the measured field strengths while disregarding field measurements associated with the distortion-contributing system element by applying to the redundant field measurements a coordinate correcting function according to a plurality of sub-volumes of the working volume that exploits the redundant location information so as to reduce an impact of the distortion on the location coordinates.

2. The method according to claim 1, and comprising inserting the object into an organ of a patient, wherein determining the position of the object comprises tracking the position of the object inside the organ.

3. The method according to claim 2, wherein the two or more field generators are associated with the object, and wherein the field sensor is located externally to the organ.

4. The method according to claim 1, wherein identifying the distortion-contributing system element comprises accepting an a-priori indication selected from a group consisting of a characteristic direction of the distortion and an identity of the distortion-contributing system element.

5. The method according to claim 1, wherein identifying the distortion-contributing system element comprises sensing a presence of the distortion in the field measurements associated with the distortion-contributing system element.

6. The method according to claim 1, wherein the distortion-contributing system element comprises a pair of one of the field sensing elements and one of the field generators.

7. The method according to claim 1, wherein disregarding the field measurements associated with the distortion-contributing system element comprises deactivating the distortion-contributing system element.

8. A system for tracking a position of an object, comprising:
    two or more field generators, which are arranged to generate respective magnetic fields in a vicinity of the object;
    a field sensor, which is associated with the object and comprises one or more field sensing elements, which is arranged to measure redundant field strengths of the magnetic fields so as to provide redundant location information of the one or more field sensing elements, wherein a measurement of at least one of the field strengths is subject to a distortion; and a processor, which is arranged to identify responsively to the measured field strengths a distortion-contributing system element, which is selected from a group consisting of the one or more field sensing elements and the two or more field generators, and to determine location coordinates of the object relative to the two or more field generators while disregarding field measurements associated with the distortion-contributing system element by applying to the redundant field strengths a coordinate correcting function according to a plurality of sub-volumes of the working volume that exploits the redundant location information so as to reduce an impact of the distortion on the location coordinates.

9. The system according to claim 8, wherein the object is adapted to be inserted into an organ of a patient, and wherein the processor is arranged to track the position of the object inside the organ.

10. The system according to claim 8, wherein the two or more field generators are associated with the object, and wherein the field sensor is located externally to the organ.

11. The system according to claim 8, wherein the processor is arranged to accept an a-priori indication selected from a group consisting of a characteristic direction of the distortion and an identity of the distortion-contributing system element.

12. The system according to claim 8, wherein the processor is arranged to identify the distortion-contributing system element by sensing a presence of the distortion in the field measurements associated with the distortion-contributing system element.

13. The system according to claim 8, wherein the distortion-contributing system element comprises a pair of one of the field sensing elements and one of the field generators.

14. The system according to claim 8, wherein the processor is arranged to deactivate the distortion-contributing system element.

15. A computer software product used in a system for tracking a position of an object, the product comprising a non-transitory computer-readable storage medium, in which program instructions are stored, which instructions, when read by the computer, cause the computer to control two or more field generators so as to generate magnetic fields in a vicinity of the object, to determine redundant field measurements using a field sensor associated with the object by accept measurements of field strengths of the magnetic fields performed by the field sensor associated with the object, wherein a measurement of at least one of the field strengths is subject to a distortion, to calculate redundant location information comprising rotation-invariant location coordinates of the object responsively to the measured field strengths, and to determine corrected location coordinates of the object by applying to the rotation-invariant location coordinates a coordinate correcting function according to a plurality of sub-volumes of a working volume that exploits the redundant location information so as to reduce an impact of the distortion on the location coordinates so as to adjust a relative contribution of each of the measured field strengths to the corrected location coordinates responsively to the distortion in the measured field strengths.

16. A computer software product used in a system for tracking a position of an object, the product comprising a non-transitory computer-readable storage medium, in which program instructions are stored, which instructions, when read by the computer, cause the computer to control two or more field generators so as to generate magnetic fields in a vicinity of the object, to determine redundant field measurements using a field sensor associated with the object by accepting measurements of field strengths of the magnetic fields performed by the field sensor, which is associated with the object and comprises one or more field sensing elements, wherein a measurement of at least one of the field strengths is subject to a distortion is used to determine redundant location information, to identify responsively to the measured field strengths a distortion-contributing system element, which is selected from a group consisting of the two or more field generators and the one or more field sensing elements, and to determine location coordinates of the object relative to the two or more field generators while disregarding field measurements associated with the distortion-contributing system element by applying to the redundant field strengths a coordinate correcting function according to a plurality of sub-volumes of the working volume that exploits the redundant location information so as to reduce an impact of the distortion on the location coordinates.

* * * * *

UNITED STATES PATENT AND TRADEMARK OFFICE
CERTIFICATE OF CORRECTION

PATENT NO. : 8,280,189 B2
APPLICATION NO. : 13/164141
DATED : October 2, 2012
INVENTOR(S) : Meir Bar-Tal and Assaf Govari It is certified that error appears in the above-identified patent and that said Letters Patent is hereby corrected as shown below:

In the Claims:

Column 20, Line 3, delete "accept" and insert -- accepting --

Signed and Sealed this
Fourteenth Day of May, 2013

Teresa Stanek Rea
*Acting Director of the United States Patent and Trademark Office*